United States Patent [19]

Fowler et al.

[11] Patent Number: 5,667,501
[45] Date of Patent: Sep. 16, 1997

US005667501A

[54] WOUND DRESSINGS

[75] Inventors: Michael Fowler, Nuneaton; Thomas Richard Burrow, Coventry; Terence Dudley Turner, Cardiff; Ryszard Jan Schmidt, Penarth; Lip Yong Chung, Cathays Cardiff, all of United Kingdom

[73] Assignee: University College Cardiff Consultants Limited, Cardiff, United Kingdom

[21] Appl. No.: 446,769

[22] PCT Filed: Dec. 3, 1993

[86] PCT No.: PCT/GB93/02490

§ 371 Date: Jun. 2, 1995

§ 102(e) Date: Jun. 2, 1995

[87] PCT Pub. No.: WO94/13333

PCT Pub. Date: Jun. 23, 1994

[51] Int. Cl.⁶ .................................................. A61F 13/00
[52] U.S. Cl. ............................ 604/304; 602/48; 602/79; 424/447

[58] Field of Search ....................... 604/304, 307, 604/368, 372; 602/41–43, 48–51; 424/616, 447, 449

[56] References Cited

U.S. PATENT DOCUMENTS 4,781,921  11/1988  Smith et al. .......................... 424/81

*Primary Examiner*—P. Zuttarelli
*Attorney, Agent, or Firm*—Kohn & Associates

[57] ABSTRACT

A wound dressing comprises a chemically modified polymer which has a free radical activity in the DPPH Test in the range 15-80 percent. It may comprise a chemically modified polymer which carries at least one chemical group which is a persistent free radical or a precursor therefor. It may comprise a chemically modified polymer which carries at least one chemical group capable of reacting with molecular oxygen in a wound environment to form hydrogen peroxide. It may comprise a chemically modified polymer capable of stimulating the activity of macrophages or the proliferation of fibroblasts or both in a wound environment.

6 Claims, No Drawings

WOUND DRESSINGS

TECHNICAL FIELD

This invention relates to dressings which provide a good healing environment for wounds.

Good wound healing is characterised by rapid and complete regeneration of the damaged tissue. Considerable efforts have been expended in the study of wound dressings with the aim of finding which dressings are most effective in promoting wound healing. The process of wound healing is complex and is not fully understood. High macrophage activity is desirable, particularly during the early stages of healing, say during the first day or so, to kill bacteria and to remove cell debris and foreign matter. This activity is generally accompanied by inflammation. High fibroblast activity is desirable, particularly during the later stages of healing, for example between the third and seventh days, to produce a high rate of regeneration.

Enhanced concentrations of active free radicals are often found in wounds, in particular small oxygen-containing free radicals such as the hydroxyl radical (OH.), the hydroperoxyl radical (OOH.) and the superoxide anion ($O_2.^-$). The latter two are in protonation equilibrium, with the anion predominating at physiological pH; the hydroperoxyl radical is a more active free radical than the superoxide anion. The presence of these radicals is believed to be advantageous in the early stages of healing, attracting macrophages into the wound and promoting the respiratory burst. Their continued presence is, however, believed to be detrimental. They are thought to promote continued inflammation and so to delay healing and in severe cases to induce tissue necrosis and permanent tissue damage. In contrast, oxidising species without unpaired electrons, such as hydrogen peroxide ($H_2O_2$), are believed to be considerably less harmful. Indeed, Burdon, Gill and Rice Evans suggest in Free Rad. Res. Commun., Vol. 7 (1989), at pages 149–159, that low levels of hydrogen peroxide (around $10-8-10^{-6}M$) stimulate fibroblast proliferation.

BACKGROUND ART

Flohé, Giertz and Bechmann discuss the use of free-radical scavengers as anti-inflammatory drugs in Handbook of inflammation, Volume 5: The Pharmacology of Inflammation, pages 255–281 (Elsevier Science Publishers BV, 1985). Superoxide anion is said to serve an indispensable purpose in the killing of phagocytosed microorganisms. Superoxide anion and reaction products such as hydroxyl radical are said to be deleterious in the extracellular environment, possibly leading to self-maintenance of the inflammatory reaction and to tissue damage. The authors report the successful treatment of a variety of inflammatory conditions by injection of the enzyme superoxide dismutase (SOD), which catalyses the reaction:

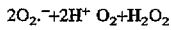

$2O_2.^- + 2H^+ \rightarrow O_2 + H_2O_2$

The authors point out a number of difficulties in the concept of scavenging free radicals by drugs rather than by enzymes. In particular, the reaction of free radical and scavenger generates a new free radical. If this is as reactive as the original radical, no benefit has been obtained. If it is less reactive, it may migrate away from the wound site and cause damage in a previously healthy area. The authors conclude that scavenging of highly reactive radicals in vivo is neither feasible nor desirable.

U.S. Pat. No. 4,837,024 describes compositions which enhance and promote the wound healing process and which comprise suspensions of the fibrous protein, collagen, and of a polysaccharide, namely a glycosaminoglycan. The glycosaminoglycan is one which exhibits chemotaxis for fibroblasts or endothelial cells; the preferred glycosaminoglycans are said to be heparin, heparan sulphate and alginate, although it should be noted that alginate is not in fact a glycosaminoglycan.

International Patent Application WO 91/11205 describes biopolymers which can be formulated into wound dressings which improve wound healing. The biopolymers are polysaccharides which contain at least 70% mannuronic acid residues, for example certain types of bacterial alginate or of oxidised guar gum or oxidised mannan.

International Patent Application WO91/12267 describes metal:peptide complexes possessing anti-oxidative and anti-inflammatory activity. The metal is typically copper (II) or manganese (II) and the peptide is a tripeptide or tetrapeptide. These soluble complexes can be used as active therapeutic substances and in the preparation of medicaments for the treatment of wounds or inflamed areas. The complexes are said to mimic the activity of SOD.

DISCLOSURE OF INVENTION

According to one aspect of the invention, a wound dressing is characterised in that it comprises a chemically modified polymer which has a free radical activity in the DPPH test as hereinafter defined in the range 15 to 80%, preferably 50 to 70%. In some cases the free radical activity of the polymer in the DPPH Test is preferably in the range 50 to 80%, more preferably 60 to 70%. In other cases, the activity is preferably in the range 15 to 70%, more preferably 15 to 50%, further preferably 25 to 40%.

According to another aspect of the invention, a wound dressing is characterised in that it comprises a chemically modified polymer which carries at least one chemical group which is a persistent free radical or a precursor therefor.

According to a further aspect of the invention, a wound dressing is characterised in that it comprises a chemically modified polymer which carries at least one chemical group capable of reacting with molecular oxygen in a wound environment to form hydrogen peroxide.

According to a further aspect of the invention, a wound dressing is characterised in that it comprises a chemically modified polymer capable of stimulating the activity of macrophages or the proliferation of fibroblasts or both in a wound environment.

By the term chemically modified polymer is meant the reaction product of a base polymer which does not carry the desired groups or have the desired activity with one or more chemical reagents to introduce the desired group or the desired activity. The base polymer carries functional groups which are capable of reacting with said reagent or reagents.

According to a further aspect of the invention, a method of wound treatment is characterised in that a wound dressing according to the invention is applied to the wound. The method further comprises applying different wound dressings according to the invention at different stages during the wound healing process.

DETAILED DESCRIPTION OF THE INVENTION

The free radical activity of a polymer can be assessed by the method herein referred to as the DPPH Test and hereinafter described under the title Test Method 1. This is a colorimetric method in which more active polymers produce a larger colour change.

Persistent free radicals can also be called stable free radicals. They are to be distinguished from active free radicals, although the distinction is only one of degree.

Hydroxyl and hydroperoxyl radicals are examples of active free radicals. They are capable of reacting with a wide variety of electron-paired molecules to form new radicals. In particular, they can abstract hydrogen atoms from electron-paired molecules as shown schematically below:

$$X^1H + OH \cdot \rightarrow X^1 \cdot + H_2O$$

$$X^1H + HOO \cdot \rightarrow X^1 \cdot + H_2O_2$$

wherein $X^1 \cdot$ represents an organic radical. The $X^1$—H bond must be somewhat labile for this reaction to take place. It is this type of reaction when $X^1H$ is a biologically important molecule that is thought to take place in an inflammatory reaction and to be responsible for the deleterious effect of these active free radicals in the later stages of the wound healing process. In contrast, persistent free radicals are generally incapable of performing such hydrogen abstractions from the sorts of molecules found in a wound environment, except when the $X^1$—H bond is very labile. Examples of highly persistent free radicals known in the field of general chemistry are the triphenylmethyl and diphenylpicrylhydrazyl (DPPH) radicals.

Certain free radicals are capable of reacting rapidly with molecular oxygen. Three examples of this type of reaction are shown schematically below:

$$X^2 \cdot + O_2 \rightarrow X^2OO \cdot$$

$$X^3H \cdot + O_2 \rightarrow X^3 \cdot + HOO \cdot$$

$$X^{4-} + O_2 \rightarrow X^4 + O_2^-$$

wherein $X^2 \cdot$, $X^3H \cdot$ and $X^{4-} \cdot$ represent organic radicals. Such reactions result in the formation of new active free radicals, which may stimulate the activity of macrophages.

Chemical groups which are precursors for persistent free radicals contain no unpaired electrons. They are capable of reacting with active free radicals to produce persistent free radicals. Polymers which carry such precursor groups are generally preferred to those which initially carry persistent free radicals, for a number of reasons. There is a wide variety of such groups, and they are generally chemically stable and easy to prepare. Suitably-chosen groups can engage in more than one free radical reaction, whereas persistent free radicals can in general engage in no more than one. In such a case, the precursor group reacts with an active free radical to form a persistent free radical, which subsequently quenches a second active free radical. Such precursor groups may engage in more than one free radical reaction in a variety of ways, depending on the chemistry of the substances involved. For example:

$$P^1 + R \cdot \rightarrow (P^1R) \cdot \qquad \text{I}$$

$$(P^1R) \cdot + R \cdot \rightarrow P^1R_2$$

$$P^2H + R \cdot \rightarrow P^2 \cdot + RH \qquad \text{II}$$

$$P^2 \cdot + R \cdot \rightarrow P^2R$$

$$P^2 \cdot + P^2 \cdot \rightarrow P^2P^2$$

$$P^3H_2 + R \cdot \rightarrow (P^3H) \cdot + RH \qquad \text{III}$$

$$(P^3H) \cdot + R \cdot \rightarrow P^3 + RH$$

In case I, a polymer $p^1$ scavenges an active-free radical R. to form a persistent free radical $(P^1R) \cdot$, which subsequently quenches another active free radical R. by addition. In case II, an active free radical R. abstracts a hydrogen atom from polymer $P^2H$ to form a persistent free radical $p^2 \cdot$ which subsequently quenches another active free radical R. or alternatively another persistent free radical $p^2 \cdot$ by addition. In case III, active free radicals R. successively abstract hydrogen atoms from a polymer $P^3H$ and from a persistent free radical $(P^3H) \cdot$. In other cases, the immediate reaction product of the precursor group and the active free radical may generate an intermediate radical which fragments to yield a persistent free radical and an electron-paired species. For example, a carboxyl radical $P^4CO_2 \cdot$ may fragment to yield a persistent free radical $p^4 \cdot$ and $CO_2$.

Certain chemical groups may reversibly dissociate to form a pair of persistent free radicals, and are thus precursors of persistent free radicals. As an example from the field of general chemistry, hexaphenylethane reversibly dissociates into two triphenylmethyl radicals.

Free radicals can in general be stabilised, and therefore made more persistent, by conjugation with unsaturated groups; and in general greater conjugation leads to greater stabilisation. Thus, again taking an example from the field of general chemistry, $NH_2 \cdot$ is a highly active free radical, $PhNH \cdot$ is much less active, while $Ph_2N \cdot$ is a well-known persistent free radical. Examples of unsaturated groups which stabilise free radicals include aromatic and heteroaromatic rings, for example azoaromatic rings, and aliphatic double bonds, for example olefinic double bonds. Groups where the unpaired electron is further delocalised over heteroatoms carrying an electron lone pair such as the oxygen atom in a hydroxy or ether group or the nitrogen atom in an amino group or over an electron-withdrawing unsaturated group such as carbonyl or imino are particularly effective at stabilising free radicals. In some cases, free radicals may also be stabilised by steric hindrance around the free radical centre.

Aromatic-aliphatic and heteroaromatic-aliphatic secondary amines are preferred examples of chemical groups which are precursors of persistent free radicals, particularly where the aromatic or heteroaromatic ring is further substituted as described above.

It was unexpected to find that polymers applied as wound dressings and remote from the wound on a molecular scale should be able to affect the wound healing process apparently through their ability to react with free radicals from the site of biological activity in the wound.

Low concentrations of hydrogen peroxide (around $10^{-8}$–$10^{-6}$M) have been shown to stimulate fibroblast proliferation. This is particularly desirable during the later stages of wound healing. Polymers that carry groups which are precursors of free radicals are often capable of reacting with molecular oxygen in a physiological environment to generate hydrogen peroxide. The process is catalysed by iron ions present at physiological concentrations. The process is believed to take the following course:

$$P^2H + O_2 \xrightarrow{Fe^{2+}/Fe^{3+}} P^2 \cdot + HOO \cdot$$

$$P^2H + HOO \cdot \rightarrow P^2 \cdot + H_2O_2$$

where $P^2H$ symbolises a polymer as before. Such polymers are of value in the wound dressings of the invention. The above process produces hydroperoxyl radical as an intermediate, and the presence of this radical is thought to delay the later stages of wound healing. However, certain polymers are capable of quenching the hydroperoxyl radical before it enters the wound environment, with the formation of hydrogen peroxide as indicated above.

Higher concentrations of hydrogen peroxide, for example $10^{-5}M$ or more, have been shown to inhibit fibroblast proliferation. Polymers which induce the formation of such higher concentrations of hydrogen peroxide in a wound environment are therefore not preferred in the wound dressings of the invention for use in the later stages of wound healing. They may be preferred for use in the earlier stages of wound healing when initiation of inflammatory activity is desired.

It is important that the polymers used in the wound dressings of the invention and their reaction products with the active free radicals found in the wound environment should not have any physiologically harmful effects. It should also be recognised that the effectiveness of any particular polymer in a wound dressing depends on the complex physiology of the wound environment, which is not fully understood. Small changes in polymer structure may have relatively large effects. In either case, theoretical predictions must always be supplemented by actual trials.

The polymer utilised in the wound dressings of the invention is manufactured by chemical modification of a base polymer carrying functional groups to introduce chemical groups which are persistent free radicals or precursors therefor. The base polymer may for example be a hydroxy-functional polymer. Examples of such polymers are polysaccharides, which may be naturally occurring or artificially modified. Further examples of such polymers are addition polymers which incorporate hydroxy-functional monomer units such as hydroxyethyl or hydroxypropyl acrylate or methacrylate.

As one example, a polymer carrying functional groups is chemically modified to introduce chemical groups which are precursors of persistent free radicals. For example, a hydroxy-functional polymer can be treated firstly with cyanuric chloride and secondly with a primary amine $RNH_2$, when it is believed that the following reactions take place:

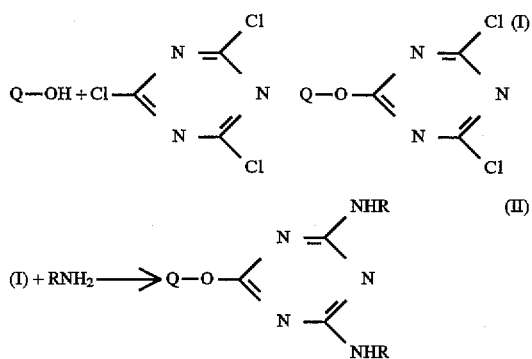

where Q represents the polymeric backbone. It is believed that hydrogen can be abstracted from an amine group in such polymers to form a persistent free radical. Suitable amines $RNH_2$ include epsilon-aminocaproic acid and glucosamine. More than one type of amine may be used, either as a mixture or by sequential addition. Alternatively, the chlorine-containing polymeric intermediate can be reacted with less than two equivalents of amine, and residual chloro groups removed by hydrolysis. This is believed to yield a polymer which contains groups of the formula:

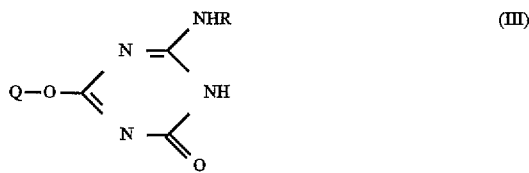

or a tautomeric form thereof.

As another example, a hydroxy-functional polymer can be caused to react with benzoquinone, oxidised, and then treated with a primary amine $RNH_2$, when it is believed that the following reactions take place:

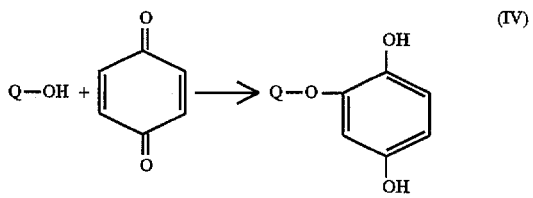

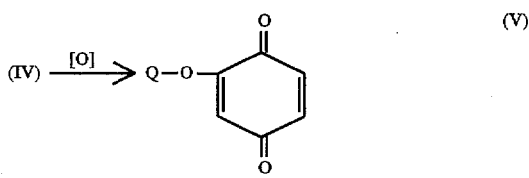

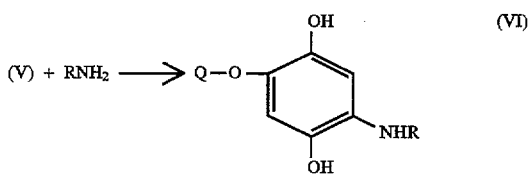

It will be observed that the intermediate (IV) possesses a hydroquinone ring. It is known that active free radicals will abstract a hydrogen atom from such a molecure to produce a persistent free radical, so that such intermediates may themselves be useful as the chemically modified polymer in the wound dressings of the invention. It will also be observed that the adduct (VI) is susceptible to free radical oxidation to a benzoquinone derivative via a persistent free radical, and that that benzoquinone derivative is itself a precursor of a persistent free radical because of the amino group attached to the ring.

As a further example, a polymer carrying reactive carbonyl groups such as aldehyde groups can be chemically modified by treatment with an amine, particularly a primary aliphatic amine. It is believed that this treatment introduces imine or enamine groups into the polymer, and that such groups are precursors of persistent free radicals at least in the case where there is an abstractable hydrogen atom in the alpha position in relation to the double bond. The mechanism of imine formation is believed to be as follows:

QCHO+RNH$_2$→QCH=NR

One suitable way of introducing aldehyde groups into a polymer is to treat an amide-functional polymer with a dialdehyde. The main reaction which occurs is believed to be as follows:

QCONH$_2$+CHOR'CHO→QCON=CHR'CHO where R' is a divalent organic group, for example an alkylene group. Examples of suitable amide-functional polymers are provided by addition polymers and copolymers of acrylamide. A particularly suitable example of a dialdehyde is glutaraldehyde. This is a readily available chemical and it has a complex chemistry which seems particularly conducive to the formation by reaction with primary amines of groups which are precursors of persistent free radicals. Glutaraldehyde can self-condense with the formation of alpha, beta-unsaturated carbonyl groups, and this extension of conjugation may be relevant in explaining this observation.

Another way of introducing aldehyde groups into a polymer is to treat a hydroxy-functional polymer with (1) a dioxirane, (2) a diamine, and (3) a dialdehyde. The following reaction scheme is proposed:

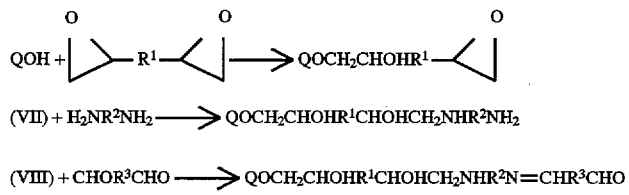

(VII) + $H_2NR^2NH_2 \longrightarrow QOCH_2CHOHR^1CHOHCH_2NHR^2NH_2$ (VIII)

(VIII) + $CHOR^3CHO \longrightarrow QOCH_2CHOHR^1CHOHCH_2NHR^2N=CHR^3CHO$ where $R^1$, $R^2$ and $R^3$ are divalent organic groups for example alkylene groups. These polymers are therefore believed to have side-chains which contain two imine groups as precursors of persistent free radicals. An example of a suitable dioxirane is butane-1,4-diol diglycidyl ether. An example of a suitable diamine is 1,2-diaminoethane. An example of a suitable dialdehyde is glutaraldehyde.

It is an advantage of the wound dressings of the invention that a wide variety of base polymers may be used and that a wide variety of chemical reagents may be used to effect chemical modification of the base polymer. This allows the preparation and use of polymers with effectively any chosen level of free radical activity.

Polymers in which the groups which are precursors of persistent free radicals are separated from the polymer backbone by a spacer group of appreciable size, for example a group whose backbone contains 6 to 20 atoms, may be desirable in the wound dressings of the invention. It is thought that the precursor groups in such polymers may be more accessible to and consequently react more readily with active free radicals from the wound environment. Examples of such polymers are provided by the case where a hydroxy-functional polymer is reacted successively with a dioxirane, a diamine, a dialdehyde, and an amine.

Addition polymers and polysaccharides which have been chemically modified to introduce groups which are precursors of persistent free radicals are particularly preferred as the polymer in the wound dressings of the invention.

The polymer may be crosslinked. This may be achieved by incorporating a small proportion of a polyfunctional monomer in the production of an addition polymer. Alternatively, a polymer carrying functional groups can be treated with a polyfunctional crosslinking agent. For example, treatment of a hydroxy-functional polymer with reagents such as cyanuric chloride or a dioxirane will generally cause some crosslinking. Crosslinking can be used as a method of adjusting the hydrophilicity of the polymer. In general, an increased degree of crosslinking corresponds to a reduced hydrophilicity. More hydrophilic polymers may be preferred in wound dressings intended for the treatment of wounds which exude appreciable amounts of fluid. It is an advantage of the wound dressings of the invention that the hydrophilicity of the polymer can be controlled independently of the control of its free radical activity.

A wound dressing material can be assessed by culturing suitable mammalian cells in the presence of the material. Materials which promote the respiratory burst of macrophages or stimulate the phagocytes are believed to be of value in the early stages of wound healing. They may also be used to induce inflammation and so stimulate healing to begin in chronic wounds such as necrotic or sloughy wounds or ulcers. A standard method of assessment of macrophage stimulation is hereinafter described as Test Method 2. Materials which stimulate the proliferation of fibroblasts are believed to be of value in the later stages of wound healing. A standard method of assessment is described hereinafter as Test Method 3.

Polymers which give a low result in the DPPH Test, that is, in the range 0 to 10%, exhibit a generally neutral behaviour, since they stimulate neither the activity of macrophages nor the proliferation of fibroblasts. Polymers which give a medium result in the DPPH Test, that is, in the range 15 to 50 or 70%, generally stimulate the activity of macrophages. Polymers which give a high result in the DPPH Test, that is, in the range 50 to 80%, generally stimulate the activity of fibroblasts. This is remarkable, in that macrophage activity is stimulated but fibroblast proliferation is suppressed by the presence of free radicals. It might therefore have been expected that polymers with medium activity would stimulate macrophages and those with high activity would stimulate fibroblasts, whereas the reverse is true.

The DPPH Test therefore gives an indication of the suitability of a wound dressing according to the invention for treating a particular type of wound or for use at a particular stage in the wound healing process. When it is desired to stimulate macrophage activity a chemically modified polymer preferably gives a DPPH Test result in the range 15 to 70%, more preferably 15 to 50%, further preferably 25 to 40%. Such polymers may be used in wound dressings according to the invention intended to stimulate inflammation and cause debriding of chronic wounds. When it is desired to stimulate fibroblast proliferation, a chemically modified polymer preferably gives a DPPH Test result in the range 50 to 80%, more preferably 60 to 70%. Such polymers may be used in wound dressings according to the invention when it is desired to promote healing without inflammation. When it is desired to stimulate both macrophage activity and fibroblast proliferation, a chemically modified polymer preferably gives a DPPH Test result in the intermediate range 50 to 70%. Such polymers may be preferred in general-purpose wound dressings according to the invention.

The wound dressings of the invention may be constructed in a variety of ways known in the art. One or more chemically modified polymers may be used. The wound dressings may additionally comprise other polymers in addition to the chemically modified polymer or polymers. For example, the chemically modified polymer may be in the form of a film which is applied directly to the wound. Alternatively, the chemically modified polymer may be a fibre in staple or continuous form, and the dressing may incorporate a fabric of such a polymer in knitted, woven or non-woven form. Alternatively, the chemically modified polymer may be applied to the wound in the form of powder or beads or as a hydrocolloid or hydrogel. Hydrocolloid and hydrogel dressings comprise a moderately or highly hydrophilic polymer, for example poly(acrylamide) or poly(ethylene oxide). The wound dressings of the invention may be medicated.

The invention also incorporates a method of treatment of a wound in which wound dressings according to the invention are applied to a wound. Different types of dressings may be applied at different stages of treatment. Typically, a dressing which promotes the activity of macrophages is used in the early stages of treatment. Such dressings may also be used to initiate the healing process in chronic wounds by stimulating inflammation. A dressing which stimulates the proliferation of fibroblasts is used once healing has commenced. This dressing might also be chosen to stimulate the activity of macrophages to some extent. Since this is generally undesirable during the later stages of healing, a dressing is used in these later stages which stimulates fibroblasts but has a minimal effect on macrophage activity. This corresponds to the use of polymers with a generally increasing DPPH Test result during the method of treatment.

The following test methods were used to assess polymers for use in the wound dressings of the invention:

Test Method 1

Free Radical Activity of Polymers (DPPH Test)

The following method was used to assess the free radical activity of polymeric materials. It is adapted from that described by M. S. Blois in Nature, Volume 181 (1958) at page 1199 and by P. W. Banda, A. E. Sherry and M. S. Blois in Analytical Letters, Volume 7 (1974) at page 41. 40 mg material was suspended in 2.5 ml distilled water. If necessary, the pH of the suspension was adjusted to 7.0 by addition of dilute HCl or NaOH. Alternatively, the material was suspended in 2.5 ml 0.1M pH 7.0 phosphate buffer. 2.5 ml methanolic $10^{-4}M$ diphenylpicylhydrazyl (DPPH) was added and the mixture was shaken and stored in the dark at 20° C. The samples were assessed by measurement of their light absorbance at 524 nm over 6 hours in comparison with a control, particular attention being paid to the figure after 4 hours. The percentage reduction in absorbance in comparison with the control after 4 hours is herein referred to as the DPPH Test. The reproducibility of the DPPH Test is of the order of ±5%.

If the polymeric material was highly swollen by or soluble in aqueous methanol, a modification of this method was used. The distilled water was substituted by 0.9% w/v saline solution. Absorbance was measured on the supernatant obtained after centrifugation at $10^4$ G for 10 min. DPPH is a well-known persistent free radical and has a strong absorption band at 524 nm. Materials with greater free radical activity have been found to induce greater and more rapid decoloration in the test described above. Polymeric materials suitable for use in the wound dressings of the invention generally produce decoloration of 15 to 80% after 4 hours.

Test Method 2

Macrophage Tests (a) Preparation of Mouse Peritoneal Exudate Cells

Quiescent macrophages were harvested from the peritoneal cavity of female WSP mice (age 6–12 wk) by washing the cavity with 3 ml of Eagles medium containing 0.5% Newborn Bovine Serum. Cells from several mice were pooled and gently centrifuged at 50 G to remove platelets. The number of nucleated cells in the lavage was determined by mixing an aliquot with white cell diluent fluid, consisting of 1% w/v gentian violet and 2% v/v acetic acid in saline, at a dilution of 1 in 10, using a white cell pipette. Following this the cells were counted using a haemacytometer. The relative percentage of macrophages in the lavage was calculated using the alpha-naphthylacetate esterase method. This method is described by Stuart, Habeshaw and Davidson in Handbook of Experimental Immunology, 2nd edition, Blackwell Scientific Publications (London). A suitable kit for carrying out the method is sold by Sigma Chemical Ltd as Research Kit 91-A. The percentage of macrophages varied between 50–65%. Before use the lavage was diluted to contain $1.5$–$2.5 \times 10^7$ cells/ml.

Quantitative Nitroblue Tetrazolium (NBT) Test. The procedure was based upon that of Baehner and Nathan, Quantitative NBT Test in Chronic Granulomatons Disease, New England J. Med., Vol 278 (1968), pages 971–976, with slight modifications to permit the testing of polymers.

Experiments were carried out in the following manner.

Control 1

To three siliconised centrifuge tubes was added Earles Balanced Salt Solution (BSS) (0.35 ml) and potassium cyanide (0.1 ml of 0.01M). Sodium chloride (0.4 ml of 0.80%) containing 0.1% NBT was also then added.

Control 2 and Experimental Tubes

To three siliconised centrifuge tubes was added BSS (0.35 ml) and potassium cyanide (0.1 ml of 0.01M). Sodium chloride (0.4 ml of 0.85%) containing, 0.1% NBT and 0.05 ml of latex particles (0.8 micron diameter) was also then added.

The above tubes were preincubated in a shaker water bath at 37° C. for 15 min. An aliquot of 0.1 ml of the macrophage suspension was added to each of the pre-incubated tubes. The incubation was allowed to run for 30 min and was terminated by adding 10 ml of 0.5N hydrochloric acid. The tubes were centrifuged at 100 G at 4° C. for 15 min. The supernatant was aspirated and the visible granular button was extracted for 10 min with 2 ml pyridine in a boiling water bath under an exhaust hood. The tubes were then centrifuged at 500 G for 10 min. A second extraction with 2 ml pyridine was then performed. The two extracts were combined and the optical density of the purple colour of the reduced NBT was determined, at 515 nm against a pyridine blank, using a PU 8620 UV Spectrophotometer.

Test Sample

To 0.1 ml of the macrophage suspension, preincubated for 30 min at 37° C. in a shaker-water bath, was added a sterilised sample of test polymer (0.1% w/v). Continual agitation of the suspension was necessary to prevent the cells from attaching to the sample polymer. A 0.1 ml aliquot of this suspension was then added to the experimental centrifuge tubes and the rest of the experiment was carried out as described above.

Results were expressed as percentage difference between the averages of the samples and the controls.

This test method allows assessment of the respiratory burst of macrophages exposed to a test polymer and so provides an indication of likely pro-inflammatory activity in the wound environment.

Test Method 3

Fibroblast Culture

L929 mouse fibroblasts were obtained from ICN Flow, High Wycombe, UK.

Complete growth medium for maintenance cultures of L929 mouse fibroblasts consisted of Minimum Essential Medium Eagle (Modified) with Earle's salts (EMEM) containing 20 mM N-2-hydroxyethylpiperazine-N'-2-ethanesulphonic acid (HEPES) supplemented with non-essential amino acids (1% v/v), 2mM L-glutamine, 100 units ml$^{-1}$ penicillin, 100 µgml$^{-1}$ streptomycin, and 10% newborn bovine serum (NBS). For experiment cultures, penicillin and streptomycin were not added to the complete growth medium.

Stock L929 cells were stored in liquid nitrogen. New cultures were initiated from frozen stock; cells were grown in sterile 75 cm$^3$ culture flasks in complete EMEM medium at 37° C. Cultures were passaged weekly and media changed three times weekly. L929 cells in the 579th and 592nd passages were used in this work.

Earle's balanced salt solution (modified) without calcium and magnesium and containing trypsin (0.25% w/v) was used in cell trypsinisation procedures. Day 0

A suspension of L929 mouse fibroblast cells (1×10$^5$ cells/ml) was prepared. Five milliliters of the suspension were added to each of a number of 25 cm$^3$ tissue culture flasks. For every experiment 3 flasks were prepared for the samples to be tested and 3 for controls. The cultures were incubated at 37° C. for 24 hours during which time the cells became attached to the surface of the flasks.

The samples to be tested were sterilised in the following manner. Beads were suspended in 70% aqueous ethanol at a concentration of 0.1% w/v and allowed to stand for 3 hours. The supernatant was then removed by decantation. Hydrophilic beads were then washed 3 times with sterile water. Hydrophobic beads were instead suspended in 95% aqueous ethanol for 1 hour. In either case the recovered beads were air-dried in a sterile cabinet.

Day 1

The suspension medium was removed from the experimental flasks and replaced by 5 ml of medium containing the sample of polymer to be tested. The medium in the control flasks was removed and replaced by 5 ml of fresh medium.

Days 3 and 6

On day 3 and on day 6 (2 and 5 days respectively from addition of the sample to be tested) three flasks containing a test sample and three controls were removed from the incubator. The flasks were briefly trypsinised to detach the cells from the flask, the sample, and each other. Trypsinisation often had to be prolonged to 20–30 minutes on day 6 if the cells had become strongly attached to the samples. Gentle shaking assisted the detachment; vigorous shaking was avoided in order to minimise damage to or lysis of the cells. Cell concentration was then measured by image-analyser-assisted or visual counting using a haemacytometer chamber as described by Turner, Spyratou and Schmidt in J. Pharm. Pharmacol., Vol. 41 (1989), at pages 775–780.

Results were expressed as percentage difference in cell concentration between the averages for the samples and the controls.

This test assesses whether a sample will stimulate fibroblast proliferation. This is desirable particularly in the later stages of wound healing, for example between the third and seventh days.

The invention is illustrated by the following Examples in which parts and proportions are by weight unless otherwise specified:

EXAMPLE 1

(a) Preparation of poly(hydroxypropyl methacrylate) beads (PHPMA beads).

A 2 L reaction flask was equipped with a Liebig condenser and a stirrer, placed in a thermostatic bath, and purged with nitrogen. A solution of 10 g poly(N-vinylpyrrolidone) (stabiliser) in 1 L water was charged into the flask. A mixture of 200 g hydroxypropyl methacrylate (monomer), 10 g ethylene glycol dimethacrylate (crosslinker) and 0.525 g azobisisobutyronitrile (initiator) was then added slowly to the stirred flask. The temperature was raised to 70° C. by means of the thermostatic bath, and the reaction mixture held at this temperature for 4 hours. Polymer beads were collected, washed to remove unreacted monomer and dried. They were then fractionated by sieving. The beads used in these Examples were generally around 100 micron in diameter.

(b) Preparation of poly(hydroxypropyl methacrylate) beads with s-triazine functionality.

1 g PHMA beads prepared as described in 1(a) was placed in a 50 ml flask together with 10 ml 12% w/v aqueous sodium hydroxide and the mixture cooled in an ice-salt bath. 4.6 g cyanuric chloride (25 mmol) was dissolved in 100 ml acetone, and the fresh solution was cooled in an ice-salt bath. A 20 ml portion of this solution was then added to the stirred suspension of beads. After 90 minutes, the mixture was removed from the ice-salt bath and allowed to stand for a further 90 minutes. The beads were then collected by filtration and washed successively with 50% aqueous acetone, acetone and water.

(c) Preparation of derivatised poly(hydroxypropyl methacrylate) beads

The treated beads as produced in 1(b) were then placed in another 50 ml flask and treated with 40 ml 0.5M aqueous phosphate buffer (pH 7.8) containing in solution 8 mmol epsilon-aminocaproic acid. The mixture was allowed to stand for 24 hours at room temperature, following which the derivatised beads were collected in the same manner as the treated beads. They were then washed with ethanol and air-dried. The beads were subjected to elemental analysis (in particular, for nitrogen) to confirm that derivatisation had taken place. These beads were given reference number 142.

Example 2

PHPMA beads with s-triazine functionality were prepared as described in Example 1(a) and (b). They were then treated as described in Example 1(c) except that D-glucosamine was substituted for epsilon-aminocaproic acid. The buffered amine solution was discarded by decantation after 24 hours and replaced by a fresh aliquot following which the reaction was allowed to proceed for a further 24 hours. The derivatised beads were collected as before.

EXAMPLE 3

Cross-linked dextran beads obtained from Pharmacia Ltd under the trade name Sephadex G25 Coarse were washed with water to remove any preservative and treated as described in Examples 1(b) and (c).

EXAMPLE 4

Cross-linked dextran beads obtained from Pharmacia Ltd under the trade name Sephadex G25 Coarse were washed with water to remove any preservative and treated as described in Examples 1(b) and 2. They were given the reference number 122.

EXAMPLE 5

(a) Reaction of dextran beads with a dioxirane 10 g dextran beads (Sephadex G25 Coarse) were washed and swollen with distilled water. The swollen beads weighed 47 g, and were placed in a flask equipped with a magnetic stirrer. The following reagents were then added sequentially: (i) 24 ml 1M NaOH; (ii) 50 mg NaBH$_4$; and (iii) 10 ml butane-1,4-diol diglycidyl ether. Stirring was continued for 5–7 hours, after which the beads were collected on a sintered funnel and washed copiously with water.

(b) Reaction of oxirane-functional beads with a diamine

The beads prepared in part (a) were added to a solution of 10 ml ethylene diamine in 40 ml distilled water. The mixture was allowed to stand overnight, after which the beads were collected on a sintered funnel and washed with water.

(c) Reaction of amine-functional beads with a dialdehyde 10 g beads from part (b) were added to 50 ml 0.5M phosphate buffer (pH 7.5). 10 ml 25% aqueous glutaraldehyde were added and the mixture incubated overnight at 40° C. The beads were then collected on a sintered funnel and washed with water until no odour of glutaraldehyde remained.

(d) Reaction of aldehyde-functional beads with an amine

The beads from part (c) were added to 100 ml 0.01M phosphate buffer (pH 7.5) containing 3.6 g D-glucosamine. The mixture was allowed to stand overnight, following which the beads were collected on a sintered funnel, washed with water and acetone, and dried in a vacuum desiccator.

Separate preparations were given the reference numbers 128 and 129.

EXAMPLE 6

Example 5 was repeated, except that the glucosamine in step (d) was replaced by epsilon-aminocaproic acid. Separate preparations were given the reference numbers 132 and 133.

EXAMPLE 7

(a) Preparation of poly(acrylamide) beads with aldehyde functionality 10 g poly(acrylamide) beads were added to 80 ml 0.5M pH 7.5 phosphate buffer. 20 ml 50% by weight aqueous glutaraldehyde solution was added to the stirred suspension which was then incubated at 40° C. overnight. The beads were then collected by filtration on a glass sinter and washed with water until free from the smell of glutaraldehyde.

(b) Reaction of aldehyde-functional beads with an amine

The beads prepared in step (a) were treated with D-glucosamine as described in Example 5(d). Separate preparations were given the reference numbers 130 and 131.

EXAMPLE 8

Poly(acrylamide) beads were treated as described in Example 7 except that in step (b) the D-glucosamine was replaced by epsilon-aminocaproic acid. Separate preparations were given the reference numbers 134 and 135.

EXAMPLE 9

Preparation of poly(hydroxypropyl methacrylate) beads with benzoquinone functionality PHPMA beads were prepared as described in Example 1(a). 1 g PHPMA beads was placed in a 50 ml flask and treated with a solution of 0.3 g (3 mmol) freshly-crystallised benzoquinone in 10 ml ethanol. 30 ml 0.5M aqueous phosphate buffer (pH 7.2) was then added to the stirred suspension. After 60 minutes at room temperature, the treated beads were collected by filtration and washed successively with 50% aqueous ethanol, ethanol, water, saline solution and water. The treated beads were reacted with epsilon-aminocaproic acid or D-glucosamine as described in Examples 1(c) and 2 respectively.

EXAMPLE 10

Polymeric materials were assessed using Test Methods 1, 2 and 3 with the following results, arranged according to the results of Test Method 1:

| Ref. Nos. | Polymer | DPPH test % | Macrophage Test | Fibroblast Test Day 3 | Fibroblast Test Day 6 |
|---|---|---|---|---|---|
| — | Cotton | 4 | — | — | — |
| — | G25 | 4 | — | — | — |
| — | G25 - Tz | 4 | — | — | — |
| 134/135 | Pac - Glt - EACA | 16 | +15 | +8 | 0 |
| 130/131 | Pac - Glt - Glm | 22 | +17 | −8 | −7 |
| 142 | PHPMA - Tz - EACA | 33 | +34 | −9 | −3 |
| 128/129 | G25 - ODG - Glm | 54 | +8 | −6 | +8 |
| 132/133 | G25 - ODG - EACA | 66 | +11 | 0 | +10 |
| 122 | G25 - Tz - Glm | 78 | — | −7 | +6 |

Abbreviations
G25      Dextran: Sephadex G25 from Pharmacia Ltd
Glm      D-glucosamine
Tz       s-triazine (reaction with cyanuric chloride)
EACA     epsilon-aminocaproic acid
ODG      Reaction with (1) butane-1,4-diol diglycidyl ether (2) 1,2-diaminoethane (3) glutaraldehyde
Pac      Poly(acrylamide)
Glt      Glutaraldehyde
LH20     Hydroxypropyldextran: Sephadex LH20 from Pharmacia Ltd.
PHPMA    Poly(hydroxypropyl methacrylate)

The effect of minor changes in polymer structure on free radical activity can clearly be seen. The best result in the macrophage test (Test Method 2) was obtained with sample 142, which gave a result in the DPPH Test (Test Method 1) of 33%. The best results in the fibroblast test (Test Method 3) after 5 days were obtained with samples 132/133, which gave a result in the DPPH Test of 66%.

What is claimed is:

1. A wound dressing which comprises an addition polymer having hydroxyl, carbonyl or amide functional groups or a polysaccharide having hydroxy functional groups, said functional groups having been converted to derivatives which are persistent free radicals or precursors of persistent free radicals, which free radicals are reactive with molecular oxygen in a mammalian wound environment comprising macrophages and/or fibroblasts, said reaction being such as to form hydrogen peroxide in said environment; wherein said polymer stimulates activity of said macrophages or proliferation of said fibroblasts in said wound environment.

2. A wound dressing according to claim 1, wherein said polysaccharide is dextran.

3. A wound dressing according claim 1, wherein said polymer is a polyacrylamide.

4. A wound dressing according to claim 1, wherein said polymer is in the form of beads.

5. A wound dressing according to claim 1, wherein, said polymer contains a chemical group which is a precursor to a persistent free radical, said chemical group being either an aromatic-aliphatic or heteroaromatic-aliphatic secondary amine.

6. A method for the treatment of a mammalian wound having a wound environment comprising macrophages and/or fibroblasts, which comprises applying to said wound at least one wound dressing according to claim 1, such that said macrophage activity is stimulated or said fibroblasts are permitted to proliferate, and said wound is permitted to heal.

* * * * *